(12) United States Patent
Seifert et al.

(10) Patent No.: US 7,254,451 B2
(45) Date of Patent: Aug. 7, 2007

(54) IMPLANTABLE LEAD INCLUDING SENSOR

(75) Inventors: Kevin R. Seifert, Forest Lake, MN (US); Teresa A. Whitman, Dayton, MN (US); Brian T. McHenry, Minneapolis, MN (US); Mark T. Marshall, Forest Lake, MN (US); Thomas S. Ahern, Coronado, CA (US)

(73) Assignee: Medtronic, Inc., Minneapolis, MN (US)

( * ) Notice: Subject to any disclaimer, the term of this patent is extended or adjusted under 35 U.S.C. 154(b) by 353 days.

(21) Appl. No.: 10/717,791

(22) Filed: Nov. 20, 2003

(65) Prior Publication Data
US 2005/0113897 A1    May 26, 2005

(51) Int. Cl.
*A61N 1/00* (2006.01)
(52) U.S. Cl. .................................. 607/127
(58) Field of Classification Search ............ 607/115, 607/116, 119, 122, 125–131
See application file for complete search history.

(56) References Cited

U.S. PATENT DOCUMENTS

| | | | |
|---|---|---|---|
| 3,942,536 A | 3/1976 | Mirowski et al. ........ | 128/419 D |
| 4,402,330 A | 9/1983 | Lindemans ................ | 128/786 |
| 4,566,456 A | 1/1986 | Koning et al. ......... | 128/419 PG |
| 4,600,017 A | 7/1986 | Schroeppel ................ | 128/784 |
| 4,730,389 A | 3/1988 | Baudino et al. ............. | 29/825 |
| 4,774,950 A | 10/1988 | Cohen .................... | 128/419 D |
| 4,791,935 A | 12/1988 | Baudino et al. ............ | 128/637 |
| 4,877,032 A | 10/1989 | Heinze et al. ........ | 128/419 PG |
| 4,984,572 A | 1/1991 | Cohen .................... | 128/419 D |
| 5,054,485 A | 10/1991 | Cohen .................... | 128/419 D |
| 5,058,586 A | 10/1991 | Heinze ...................... | 128/634 |
| 5,083,563 A | 1/1992 | Collins .................... | 128/419 D |
| 5,085,213 A | 2/1992 | Cohen .................... | 128/419 D |
| 5,105,810 A | 4/1992 | Collins et al. .......... | 128/419 D |
| 5,184,614 A | 2/1993 | Collins et al. ........ | 128/419 PG |
| 5,271,392 A * | 12/1993 | Ferek-Petric .................. | 607/14 |
| 5,324,326 A | 6/1994 | Lubin ........................ | 607/122 |
| 5,545,205 A * | 8/1996 | Schulte et al. ............... | 607/123 |
| 5,564,434 A | 10/1996 | Halperin et al. ............. | 607/748 |
| 5,999,838 A | 12/1999 | Crowley et al. ............ | 600/410 |
| 6,201,994 B1 * | 3/2001 | Warman et al. ............. | 607/123 |
| 6,256,542 B1 | 7/2001 | Marshall et al. ............ | 607/126 |
| 6,505,082 B1 * | 1/2003 | Scheiner et al. ............ | 607/123 |
| 2003/0199957 A1 | 10/2003 | Struble et al. .............. | 607/122 |

FOREIGN PATENT DOCUMENTS

EP    0 656 218 B1    4/2002
WO    WO 99/53993 A1    10/1999

* cited by examiner

*Primary Examiner*—George Manuel
(74) *Attorney, Agent, or Firm*—Carol F. Barry; Girma Wolde-Michael

(57) ABSTRACT

An implantable lead includes a defibrillation electrode and a sensor coupled thereto. The electrode and sensor are positioned along a body of the lead such that, when a fixation element couples the lead to an endocardial surface of a right ventricle, the sensor is located in a high flow region and a portion of the defibrillation electrode is located in proximity to a right ventricular apex.

30 Claims, 8 Drawing Sheets

IMPLANTABLE LEAD INCLUDING SENSOR

TECHNICAL FIELD

The present invention relates to implantable medical electrical leads and more particularly to leads including a stimulating electrode and a physiological sensor and the arrangements thereof along a body of the leads.

BACKGROUND

Cardiac rhythm management (CRM) systems often employ an implantable medical device (IMD) coupled to an endocardial surface of a patient's right heart via one or more medical electrical leads. Typically the one or more leads include electrodes for both stimulating the heart and sensing electrical activity of the heart. In order to provide better management of cardiac conditions, the one or more leads may also include a physiological sensor. In many cases, it is desirable that all the necessary electrodes and a physiological sensor be carried on a single lead body wherein locations of each electrode and the sensor along the lead body accommodate proper function of the lead to meet the therapeutic objectives of the CRM system. For example, it is important to position certain types of physiological sensors in high flow regions of the right heart; examples of these types of sensors, well known to those skilled in the art, include oxygen sensors, pressure sensors, temperature sensors and flow sensors.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and:

FIGS. 6A-7B are partial plan views of distal portions of leads according to further alternate embodiments of the present invention.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1A:
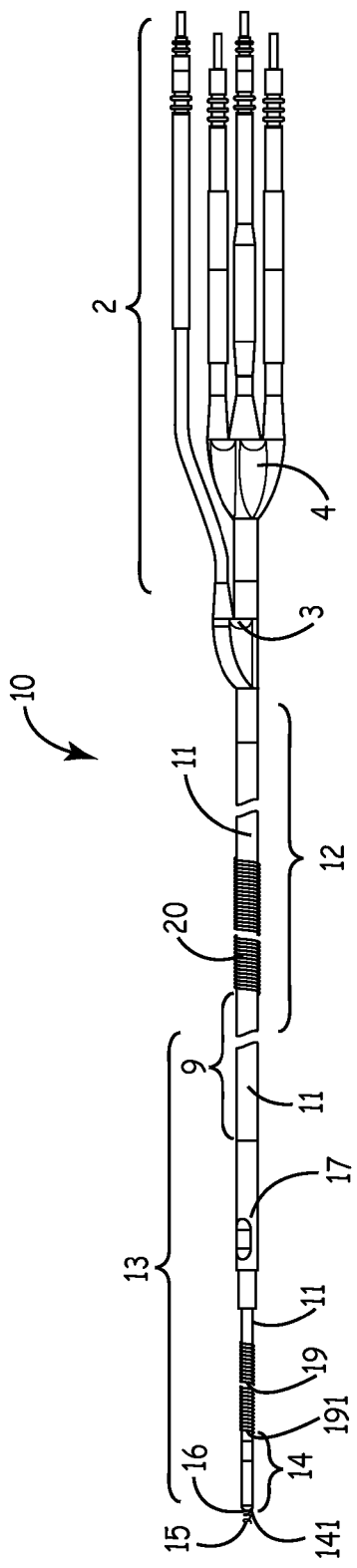
FIGS. 1A-B are plan views of medical electrical leads according to alternate embodiments of the present invention.
Figure 1B:
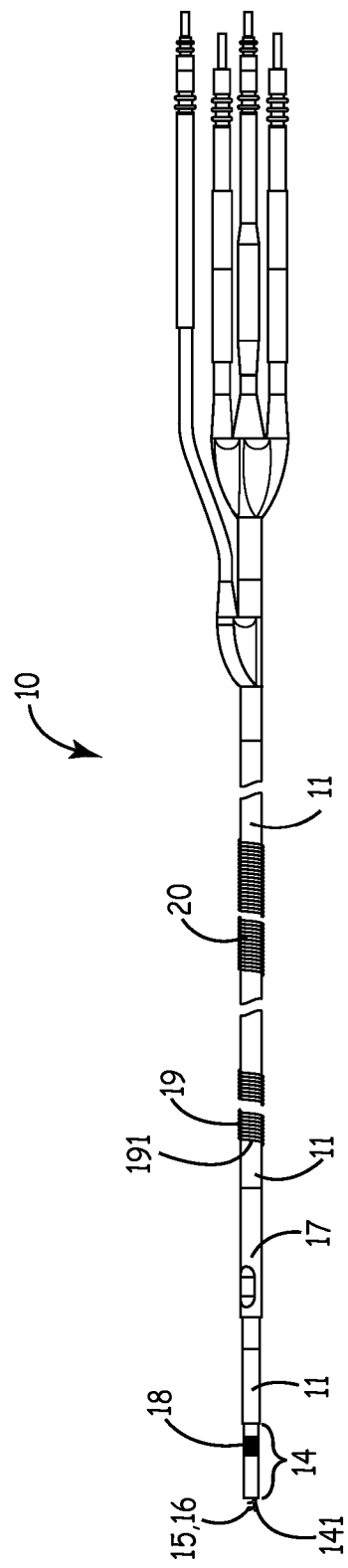
Figure 3:
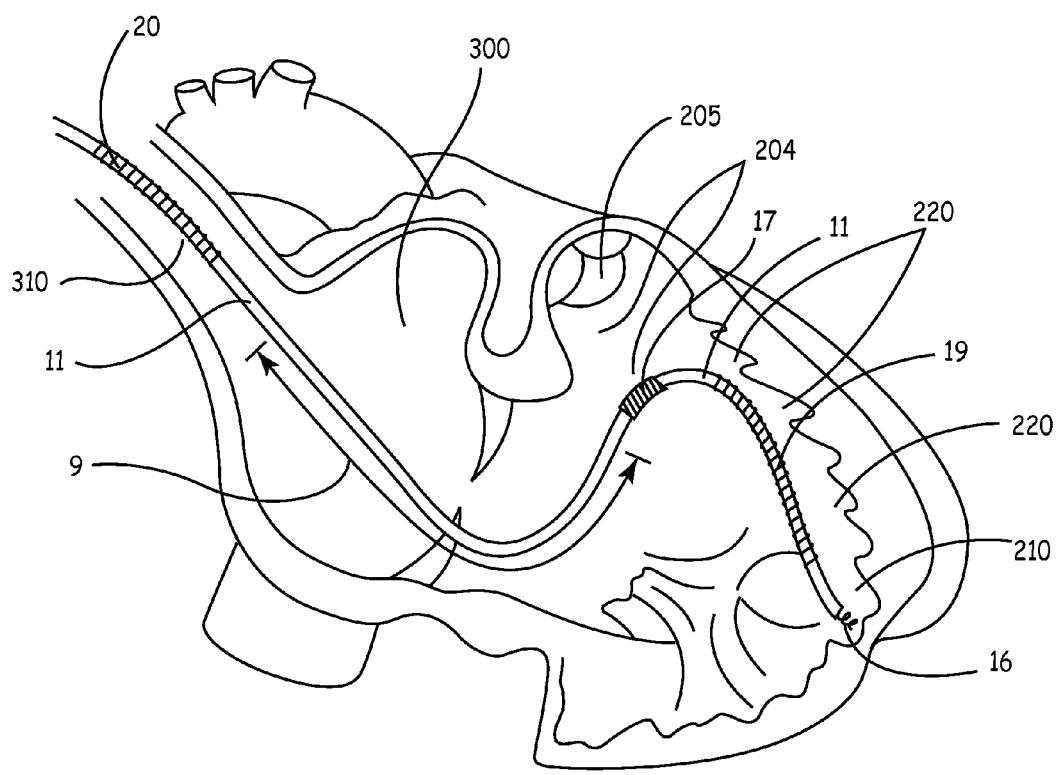
FIGS. 3-5 are schematic views of the right heart depicted in FIG. 2 including alternate embodiments of leads implanted therein.

FIGS. 1A-B are plan views of medical electrical leads according to alternate embodiments of the present invention. FIG. 1A illustrates a lead 10 including a lead body 11 having a proximal portion 12 and a distal portion 13; distal portion 13 includes a distal tip 14, to which a fixation element 15 and a cathode tip electrode 16 are coupled, a defibrillation electrode 19 positioned proximal to distal tip 14 and a sensor 17 positioned proximal to defibrillation electrode 19. FIG. 1B illustrates a lead 100 also including lead body 11, however, according to this embodiment, sensor 17 is positioned distal to defibrillation electrode 19 and distal tip 14 further includes an anode ring electrode 18 and cathode tip electrode 16 is combined into fixation element 15. Appropriate cathode electrode, anode electrode and defibrillation electrode designs known to those skilled in the art may be incorporated into embodiments of the present invention. Although FIGS. 1A-B illustrate proximal portion 12 including a second defibrillation electrode 20, embodiments of the present invention need not include second defibrillation electrode 20. For those embodiments including defibrillation electrode 20, electrode 20 is positioned along lead body such that electrode 20 is located in proximity to a junction between a superior vena cava 310 and a right atrium 300 when distal portion 13 of lead body 11 is implanted in a right ventricle 200 (FIG. 3). Additionally, tip electrode 16 and ring electrode 18 are not necessary elements of embodiments of the present invention.

FIGS. 1A-B illustrate fixation element 15 as a distally extending helix, however element 15 may take on other forms, such as tines or barbs, and may extend from distal tip 14 at a different position and in a different direction, so long as element 15 couples lead body 11 to an endocardial surface of the heart in such a way to accommodate positioning of defibrillation electrode 19 and sensor 17 appropriately, as will be described in conjunction with FIGS. 2-5.

According to alternate embodiments of the present invention, sensor 17 is selected from a group of physiological sensors, which should be positioned in high flow regions of a circulatory system in order to assure proper function and long term implant viability of the sensor; examples from this group are well known to those skilled in the art and include, but are not limited to oxygen sensors, pressure sensors, flow sensors and temperature sensors. Commonly assigned U.S. Pat. No. 5,564,434 describes the construction of a pressure and temperature sensor and means for integrating the sensor into an implantable lead body. Commonly assigned U.S. Pat. No. 4,791,935 describes the construction of an oxygen sensor and means for integrating the sensor into an implantable lead body. The teachings U.S. Pat. Nos. 5,564,434 and 4,791,935, which provide means for constructing some embodiments of the present invention, are incorporated by reference herein.

FIGS. 1A-B further illustrates lead body 11 joined to connector legs 2 via a first transition sleeve 3 and a second transition sleeve 4; connector legs 2 are adapted to electrically couple electrodes 15, 16, 19 and 20 and sensor 17 to an IMD in a manner well known to those skilled in the art. Insulated electrical conductors, not shown, coupling each electrode 15, 16, 19 and 20 and sensor 17 to connector legs 2, extend within lead body 11. Arrangements of the conductors within lead body 11 include coaxial positioning, non-coaxial positioning and a combination thereof; according to one exemplary embodiment, lead body 11 is formed in part by a silicone or polyurethane multilumen tube, wherein each lumen carries one or more conductors.

Figure 2:
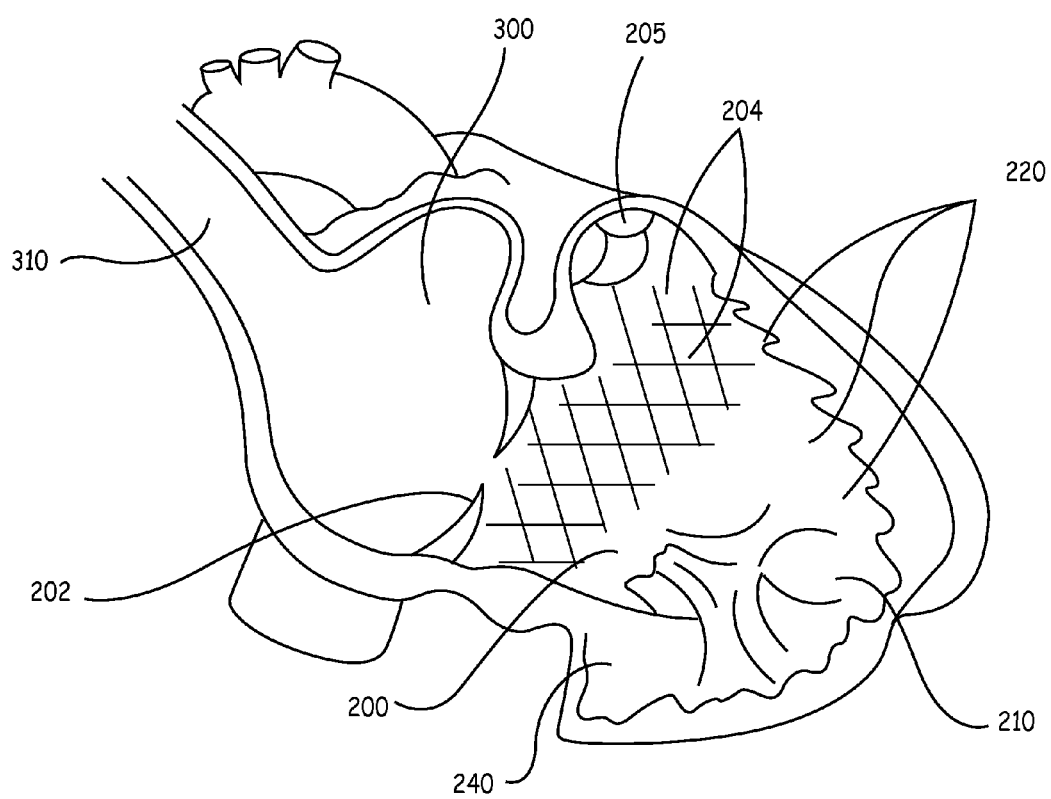
FIG. 2 is a schematic view of an inside of a right heart.

FIG. 2 is a schematic view of an inside of a right heart. FIG. 2 illustrates a tricuspid valve (TV) 202 above a right ventricle (RV) 200, a lateral free wall 240 of RV 200 (peeled back), an RV apex 210, a septal/anterior free wall groove 220 and an RV outflow tract (RVOT) 204 leading to a pulmonary valve (PV) 205. According to the present invention a cross-hatched zone within RV 200 represents a high flow region defined by a 3 dimensional space in an upper portion of RV 200, below TV 202 and along RVOT 204; embodiments of the present invention, for example leads 10, 100, include a sensor positioned along a lead body such that the sensor is located somewhere in the high flow region when the lead is implanted. Blood flow through the right heart is well known to those skilled in the art and need not be detailed herein.

Figure 4:
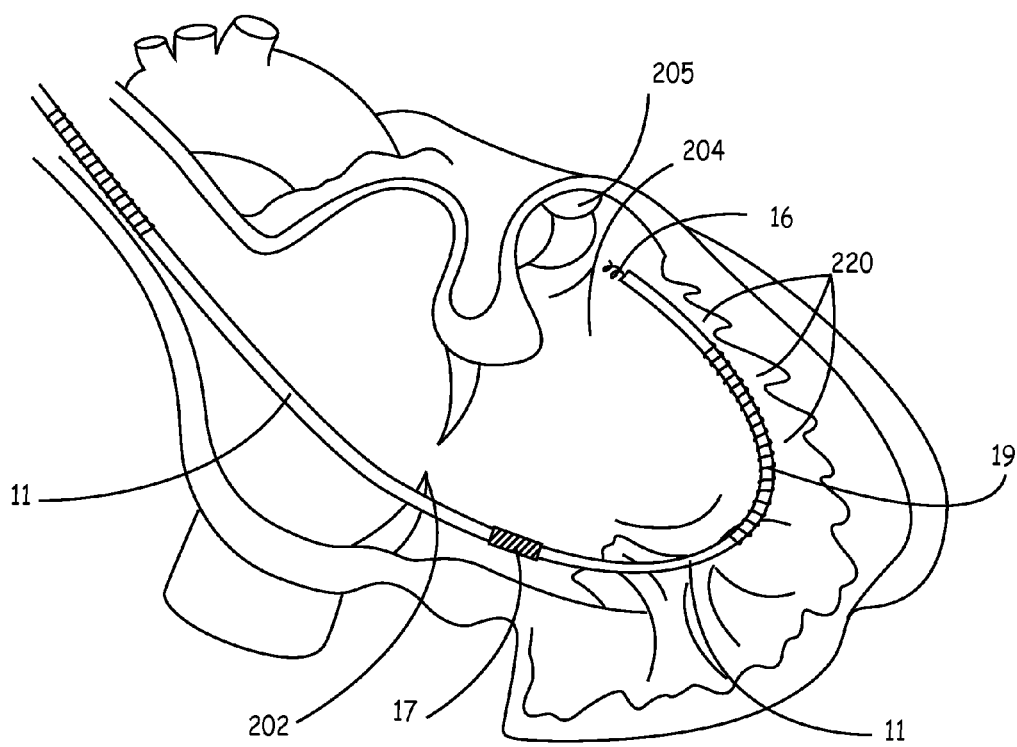
Figure 5:
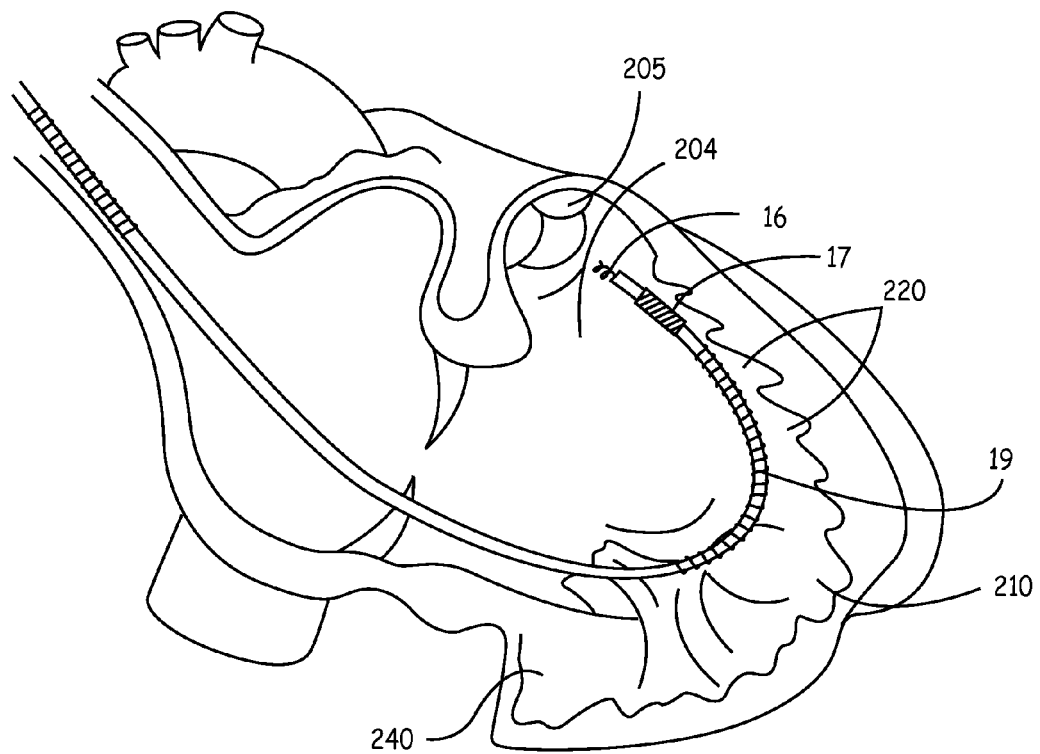

FIGS. 3-5 are schematic views of the right heart depicted in FIG. 2 including alternate embodiments of leads implanted therein. FIG. 3 illustrates lead body 11, for example of lead 10 illustrated in FIG. 1A, implanted in RV 200 with fixation element 16 coupled to an endocardial surface in proximity to RV apex 210; a portion of defibrillation electrode 19 extends approximately along septal/free wall groove 220 and sensor 17 is located in a portion of the high flow region (FIG. 2) along RVOT 204. FIG. 4 illustrates an alternate implant position for lead body 11 wherein fixation element 16 is coupled to the endocardial surface in proximity to RVOT 204; a portion of defibrillation electrode 19 extends approximately along septal/free wall groove 220, but in this case, sensor 17 is located in another portion of the high flow region that is below TV 202.

FIG. 5 illustrates lead body 11, for example of lead 100 illustrated in FIG. 1B, implanted in RV 200 with fixation element 16 coupled to an endocardial surface in proximity to RVOT 204; a portion of defibrillation electrode 19 extends approximately along lateral free wall 240 and sensor 17 is located in a portion of the high flow region (FIG. 2) along RVOT 204.

Positions of sensor 17 and defibrillation electrode 19 along lead body, according to embodiments of the present invention, accommodate both a location of sensor 17 in the high flow region and a location of a portion of electrode 19 near RV apex 210. Referring to FIG. 1A in conjunction with FIGS. 3 and 4, according to alternate embodiments of the invention, pressure sensor is positioned along lead body 11 at a distance in a range of approximately 8 cm to approximately 12 cm from a distal end 141 of distal tip 14, and a distal end 191 of defibrillation electrode 19 is positioned at a distance in a range of approximately 8 mm to approximately 14 mm from distal end 191; an intended location along an endocardial surface, for coupling of fixation element 16, and a length of defibrillation electrode 19 may impact an exact position of these elements along lead body 11. Referring to FIG. 1B in conjunction with FIG. 5, according to further alternate embodiments of the invention, pressure sensor is positioned along lead body 11 at a distance in a range of approximately 2 cm to approximately 5 cm from a distal end 141 of distal tip 14, and a distal end 191 of defibrillation electrode 19 is positioned at a distance in a range of approximately 5 cm to approximately 8 cm from distal end 141.

FIG. 3 further illustrates a length 9 of lead body 11 extending from proximal portion 12 to distal portion 13 (FIG. 1A), which, according to one embodiment of the present invention, includes a stiffening member to aid in pushing lead body 11 into the illustrated position and buttressing lead body 11 in order to hold sensor 17 and defibrillation electrode 19 in the position once the lead is implanted. One example of a stiffening member suitable for this purpose is a tube of polyurethane overlaying lead body 11 along length 9; other examples include an element inserted within lead body 11 or a stiffened portion of one of the conductors extending along length 9. Length 9 may extend from sensor 17 to defibrillation electrode 20 or may only extend from sensor 17, proximally, far enough to achieve the illustrated position.

Figure 6A:
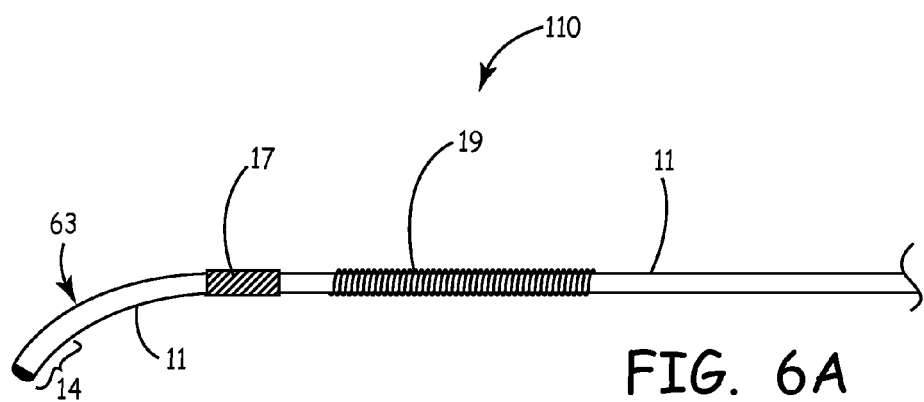
Figure 6B:
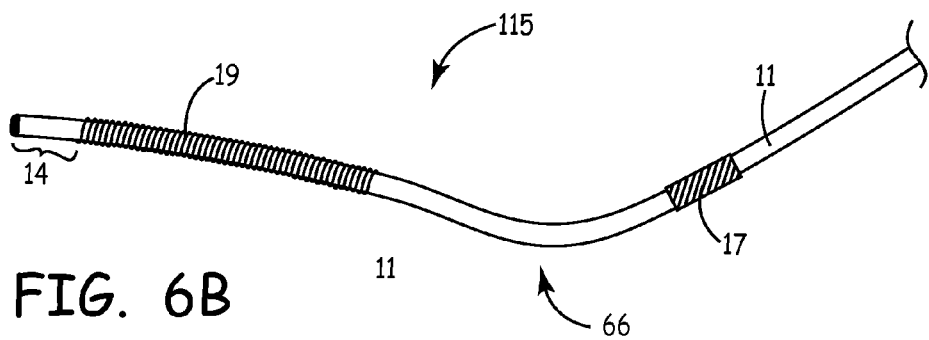
Figures 7A, 7B:
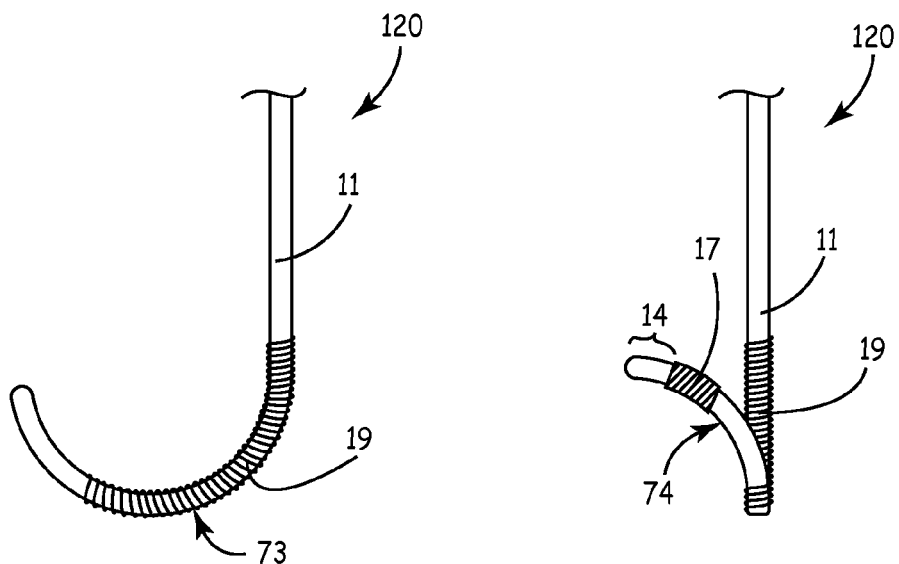

FIGS. 6A-7B are partial plan views of distal portions of leads according to further alternate embodiments of the present invention wherein preformed bends are incorporated to aid in positioning the leads within RV 200. FIG. 6A illustrates a distal portion 110 of lead body 11 including a preformed bend 63 positioned between distal tip 14 and sensor 17; bend 63 may aid in directing distal tip 14 toward an endocardial surface in RVOT 204, for example as illustrated in FIG. 5 where fixation element 16 would be directed into the page. FIG. 6B illustrates a distal portion 115 of lead body 11 including a preformed bend 66 positioned between pressure sensor 17 and defibrillation electrode 19; bend 66 may aid in directing and holding distal portion 115 within RV 200 such as is illustrated in FIG. 3. FIGS. 7A-B illustrate a distal portion 120 of lead body 11 from a side and an end, respectively, wherein a first curve 73 and a second curve 74 are pre-formed in lead body 11. Preformed first and second curves 73, 74 may aid in directing and holding distal portion 120 in RV 200 such as is illustrated in FIG. 5 where fixation element 16 would be directed into the page. According to an alternate embodiment second preformed curve 74 directs distal tip 14 in an opposite direction to that illustrated in FIG. 7B. Means for pre-forming curves 63, 66, 73 and 74 are well known to those skilled in the art of lead construction, examples of which include incorporating a preformed resilient coiled member, a preformed segment of polymer tubing or a molded polymer component into or around lead body 11.

Figure 8:
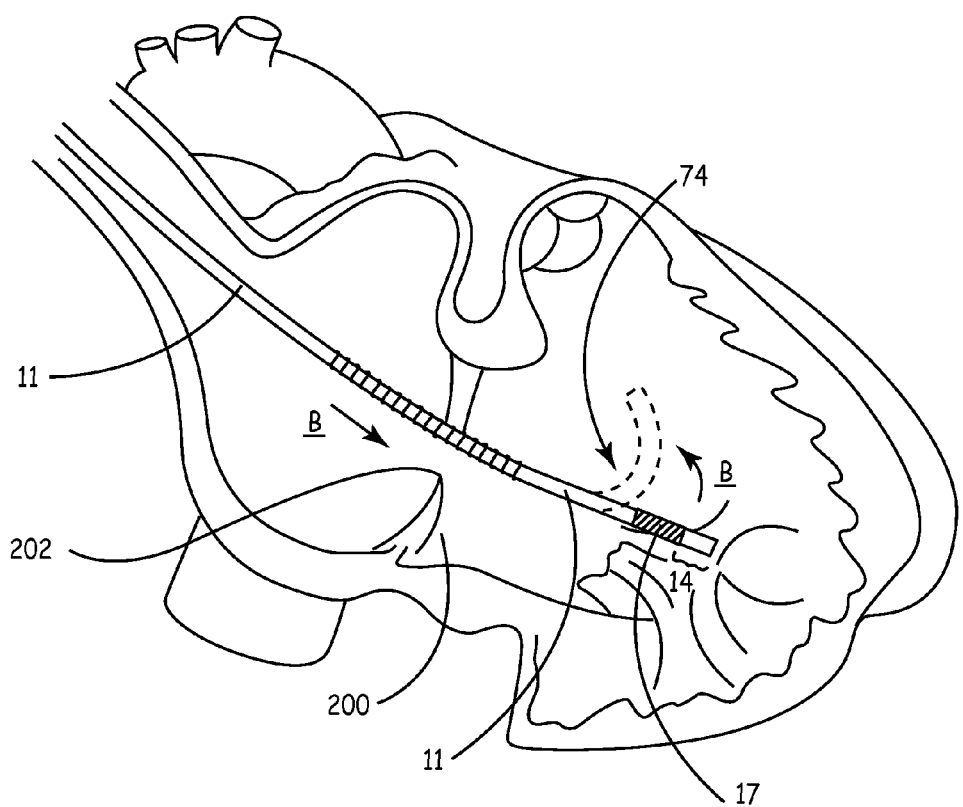
FIG. 8 is a schematic depicting steps of a method for implanting a lead according to one embodiment of the present invention.

FIG. 8 is a schematic depicting steps of a method for implanting a lead according to one embodiment of the present invention. FIG. 8 illustrates a distal portion of a lead body, for example distal portion 120, from FIGS. 7A-B, straightened by an internal stylet wire (not shown) and advanced within RV 200 per arrow A; once distal tip 14 is well within RV 200, the stylet is retracted to allow lead body 11 to bend, shown by dashed lines, per arrow B into preformed curve 74. Referring now to FIG. 5, stylet is further withdrawn and lead body 11 further advanced in order to position lead so that fixation member 16 may be coupled to an endocardial surface in RVOT 204 with defibrillation coil 19 draped in RV apex 210; preformed curve 73 (FIG. 7A) may facilitate such a positioning.

In the foregoing detailed description, the invention has been described with reference to specific embodiments. However, it may be appreciated that various modifications and changes can be made without departing from the scope of the invention as set forth in the appended claims.

What is claimed is:

1. An implantable defibrillation lead, comprising:
   a lead body including a distal portion terminated by a distal tip, the distal tip including a fixation element coupled thereto, the fixation element adapted to couple the lead to an endocardial surface of a right ventricle;
   a defibrillation electrode coupled to the distal portion of the lead body and positioned along the distal portion of the lead body such that a portion of the electrode being located in proximity to a right ventricular apex when the fixation element couples the lead to the endocardial surface; and
   a physiological sensor adapted to function in a high flow region of a circulatory system coupled to the distal portion of the lead body for sensing signals other than cardiac electrical signals, the sensor positioned along the distal portion of the lead body such that the sensor being located in a high flow region of the right ventricle and spaced apart from the endocardial surface when the fixation element couples the lead to the endocardial surface.

2. The implantable lead of claim 1, wherein
the sensor being positioned proximal to the defibrillation electrode; and
when the fixation element couples the lead to the endocardial surface in proximity to the right ventricular apex, another portion of the defibrillation electrode extends approximately along a septal/anterior free wall groove of the right ventricle.

3. The implantable lead of claim 2, wherein
the distal tip further includes a pacing electrode; and
a distal end of the defibrillation electrode being positioned at a distance in a range of approximately 8 mm to approximately 14 mm from the pacing electrode.

4. The implantable lead of claim 1, wherein
the sensor being positioned proximal to the defibrillation electrode; and
when the fixation element couples the lead to the endocardial surface along a right ventricular outflow tract, another portion of the defibrillation electrode extends approximately along a septal/anterior free wall groove of the right ventricle.

5. The implantable lead of claim 1, wherein
the sensor being positioned distal to the defibrillation electrode; and
when the fixation element couples the lead to the endocardial surface along a right ventricular outflow tract, another portion of the defibrillation electrode being located in proximity to a lateral free wall of the right ventricle.

6. The implantable lead of claim 5, wherein a distal end of the defibrillation electrode being positioned at a distance in a range of approximately 5 cm to approximately 8 cm from a distal end of the distal tip.

7. The implantable lead of claim 1, wherein the sensor being positioned at a distance in a range of approximately 8 cm to approximately 12 cm from a distal end of the distal tip.

8. The implantable lead of claim 7, wherein the distance being in a range of approximately 10 cm to approximately 12 cm.

9. The implantable lead of claim 1, wherein the sensor being positioned at a distance in a range of approximately 2 cm to approximately 5 cm from a distal end of the distal tip.

10. The implantable lead of claim 9, wherein the distance being in a range of approximately 3 cm to approximately 5 cm.

11. The implantable lead of claim 1, wherein the distal tip further includes a pair of pacing electrodes, the pair including an anode and a cathode.

12. The implantable lead of claim 1, wherein the lead body further includes a proximal portion and further comprising a second defibrillation electrode coupled to the proximal portion of the lead body and, when the fixation element couples the lead to the endocardial surface, the second defibrillation electrode being located in proximity to a junction of a superior vena cava and an right atrium.

13. The implantable lead of claim 1, wherein the high flow region being defined below a tricuspid valve.

14. The implantable lead of claim 1, wherein the high flow region being defined along a right ventricular outflow tract.

15. The implantable lead of claim 1, wherein the lead body further includes a pre-formed bend positioned in between the sensor and the distal tip.

16. The implantable lead of claim 1, wherein the lead body further includes a preformed bend positioned in between the sensor and the defibrillation electrode.

17. The implantable lead of claim 16, wherein the lead body further includes second preformed bend positioned within a length of the defibrillation electrode.

18. The implantable lead of claim 17, wherein the second preformed bend being out of plane from the preformed bend positioned in between the sensor and the defibrillation electrode.

19. The implantable lead of claim 2, wherein the lead body further includes a stiffening member extending proximally from the sensor.

20. The implantable lead of claim 19, wherein the stiffening member comprises a tube overlaying the lead body.

21. The implantable lead of claim 20, wherein the tube being formed of a material comprising polyurethane.

22. A method for implanting a lead, which includes a defibrillation electrode and a physiological sensor adapted to function in a high flow region of a circulatory system coupled to a body of the lead body for sensing signals other than cardiac electrical signals, the method comprising the step of positioning a distal portion of the lead body within a right ventricle such that a portion of the defibrillation electrode being positioned in proximity to an apex of the right ventricle and the sensor being positioned in a high flow region of the right ventricle and spaced apart from the endocardial surface.

23. The method of claim 22, wherein the high flow region being defined below a tricuspid valve.

24. The method of claim 22, wherein the high flow region being defined along a right ventricular outflow tract.

25. The method of claim 22, wherein another portion of the defibrillation electrode being positioned in proximity to a septal/anterior free wall groove of the right ventricle.

26. The method of claim 22, wherein another portion of the defibrillation electrode being positioned in proximity to a lateral free wall of the right ventricle.

27. The method of claim 22, further comprising the step of coupling the lead, via a fixation element coupled to a distal tip of the lead, to an endocardial surface of the right ventricle located in proximity to the apex of the right ventricle.

28. The method of claim 22, further comprising the step of coupling the lead, via a fixation element coupled to a distal tip of the lead, to an endocardial surface of the right ventricle located in proximity to an outflow tract of the right ventricle.

29. The method of claim 22, wherein the step of positioning comprises:
advancing a distal tip of the lead body toward an apex of the right ventricle;
withdrawing a stylet from within a distal portion of the lead body to allow a pre-formed curve of the lead body to bend;
pushing the lead body further into the right ventricle while further withdrawing the stylet to allow a second pre-formed curve of the lead body to bend.

30. An implantable defibrillation lead, comprising:
a lead body including a distal portion terminated by a distal tip, the distal tip including a fixation element coupled thereto, the fixation element adapted to couple the lead to an endocardial surface of a right ventricle;
a defibrillation electrode coupled to the distal portion of the lead body and positioned along the distal portion of the lead body such that a portion of the electrode being located in proximity to a right ventricular apex when the fixation element couples the lead to the endocardial surface; and a pressure sensor coupled to the distal portion of the lead body and adapted to function in a high flow region of a circulatory system, the sensor positioned along the distal portion of the lead body such that the sensor being located in a high flow region of the right ventricular chamber and spaced apart from the endocardial surface when the fixation element couples the lead to the endocardial surface.

* * * * *